United States Patent [19]
Godfrey et al.

[11] Patent Number: 5,858,798
[45] Date of Patent: Jan. 12, 1999

[54] METHOD AND APPARATUS FOR DETECTING AMINES AND AMMONIA BY FLUORESCENCE

[75] Inventors: Martin R. Godfrey, Elburn; Donald E. Govoni, Joliet; Linda M. Link, Carol Stream, all of Ill.

[73] Assignee: Nalco Chemical Company, Naperville, Ill.

[21] Appl. No.: 679,477

[22] Filed: Jul. 12, 1996

[51] Int. Cl.$^6$ ..................................... G01N 33/00
[52] U.S. Cl. .................. 436/113; 422/3; 422/11; 422/12; 422/13; 422/14; 422/15; 422/16; 422/17; 422/18; 422/19; 422/119; 436/6; 436/96; 436/109; 436/111; 426/112
[58] Field of Search .................... 422/3, 11, 12, 422/13, 14, 15, 16, 17, 18, 19, 119; 436/6, 96, 109, 111, 112, 113

[56] References Cited

U.S. PATENT DOCUMENTS

| | | | |
|---|---|---|---|
| 4,837,166 | 6/1989 | de Montigny et al. | 436/111 |
| 4,910,314 | 3/1990 | de Mostigny et al. | 548/110 |
| 4,992,380 | 2/1991 | Moriarty et al. | 436/55 |
| 5,411,889 | 5/1995 | Hoots et al. | 436/6 |
| 5,418,170 | 5/1995 | Rounbehler et al. | 436/111 |
| 5,435,969 | 7/1995 | Hoots et al. | 422/12 |

OTHER PUBLICATIONS

Hitachi K.K., Derwent 86–071856/11, 1986.
Bernstein, D., Chem. Abst. 90:80417, 1978.
Reagents for Modifying Amines, Alcohols, Arginine and Guanosine, Molecular Probes, Inc., Set 7, pp. 36–37.
Amino Acid Analysis with o–Phthalaldehyde Detection: Effects of Reaction Temperature and Thiol on fluorescence Yields, Conin/Pizzarello/Gandy, Analytical Biochemistry 93, 174–179 (1979).
Fluorometric Measurement of Aqueous Ammonium Ion in a Flow Injection System, Genfa/Dasgupta, Anal. Chem. 1989, 61, 408–412.
Determination of Amines in Indoor Air from Steam Humidification, Edgerton/Kenny/Joseph, Enviro. Sci. Technol., vol. 23, No. 4, 1989, pp. 484–488.

*Primary Examiner*—Peter O'Sullivan
*Attorney, Agent, or Firm*—Margaret M. Brumm; Thomas M. Breininger

[57] ABSTRACT

Primary amines, ammonia, or mixtures thereof can be detected using a reagent comprising from about 650 ppm to about 25 percent by weight of phthalic dicarboxyaldehyde; from about 74 to about 99.88 percent by weight of an alkali metal borate; and, from about 550 ppm to about 22 percent by weight of a nucleophile.

18 Claims, 6 Drawing Sheets

METHOD AND APPARATUS FOR DETECTING AMINES AND AMMONIA BY FLUORESCENCE

BACKGROUND OF THE INVENTION

1. Field of the Invention

The field of technology of the invention is the treatment of fluid systems wherein corrosive conditions may exist, and more specifically, the detection of primary amines or ammonia in such fluid systems.

2. Description of the Prior Art

The uses of steam include comfort heating, hot water heating, food services, humidification, sterilization, and laundry services. Direct steam injection can be used to humidify room air or to heat liquids or objects. More commonly, the steam flows through a heat exchanger and transfers energy to another fluid without making direct contact with that fluid. The term condensate refers to steam that has condensed to the liquid state (water) during the heat exchange process. Condensate is commonly collected through a system of tanks, traps, and receivers so that it can be returned to the boiler and used as feed water.

Boiler feed water typically consists of both make-up water and returned condensate. The make-up water is generally purified water from a primary source such as a city water system, a well, or a river. Make-up water replaces hydraulic losses in the boiler system such as steam that was not returned as condensate. Another major hydraulic loss is boiler blowdown or water that is released from the boiler itself. Blowdown is necessary to limit the concentration of dissolved solids in the boiler water. A primary objective in the successful operation of any steam generating system is to maximize its overall efficiency and reliability while minimizing problems related to water and steam quality. One of the greatest factors in achieving this objective is the amount and purity of condensate returned to the boiler as feed water. Returned condensate, being condensed steam, is extremely pure and has a relatively high heat content, making it ideal for boiler feed water.

As more condensate is returned, less make-up water is required, thereby saving on both water and pretreatment costs. Since condensate is already hot (typically between 180° and 200° F.), less fuel is required to convert it into steam. The high purity of condensate reduces the need for boiler blowdown, thereby reducing water, energy, and chemical loss. The overall scale-forming tendency of the boiler water is also reduced by condensate return and results in cleaner heat transfer surfaces.

While the use of high purity hot condensate contributes to the efficiency of steam generating equipment, the presence of very small amounts of contaminants in the liquid condensate can cause damaging corrosion of most ferrous and nonferrous metals in the condensate system, including piping and equipment. When metal oxide corrosion products formed in the condensate system are returned to the boiler they have a strong propensity to deposit on the heat transfer surfaces. This deposition limits heat transfer efficiency in the boiler and can initiate under-deposit corrosion mechanisms. Therefore, there is a strong desire to limit corrosion in boiler condensate systems.

The major causes of corrosion are dissolved gases such as carbon dioxide ($CO_2$) and oxygen ($O_2$). Oxygen is present due to air leakage into the condensate system components and can be excluded by good design and maintenance practices. The major source of $CO_2$ in the steam is the thermal breakdown of bicarbonate and carbonate alkalinity present in the feed water. At boiler operational temperatures and pressures, the following alkalinity reactions occur:

$$2\ NaHCO_3 \rightarrow Na_2CO_3 + CO_2 + H_2O \quad \text{(Equation 1)}$$

$$Na_2CO_3 + H_2O \leftrightharpoons 2\ NaOH + CO_2 \quad \text{(Equation 2)}$$

The breakdown of the bicarbonates (see Equation 1) proceeds to 100% completion. Carbonate breakdown (see Equation 2) proceeds from about 70 to about 100% completion, depending on the boiler pressure. The $CO_2$ liberated in both reactions is carried with the steam and dissolves in the condensate. As it dissolves, it forms carbonic acid:

$$CO_2 + H_2O \leftrightharpoons H_2CO_3 \leftrightharpoons H^+ + HCO_3^- \quad \text{(Equation 3)}$$

Since condensate is extremely pure, even small quantities of carbonic acid can significantly lower condensate pH and correspondingly increase its corrosivity. As little as 1 ppm of $CO_2$ in the steam can depress the pH of the condensate to 5.5. High alkalinity feed water will produce very corrosive condensate.

The corrosion reaction of carbonic acid with iron produces ferrous bicarbonate, $Fe(HCO_3)_2$, and hydrogen gas:

$$Fe + 2H^+ + 2\ HCO_3^{-2} \rightarrow Fe(HCO_3)_2 + H_2 \quad \text{(Equation 4)}$$

The soluble ferrous bicarbonate is carried away with the condensate, leaving behind an area of obvious metal loss. The corrosion usually appears as a uniform attack leaving a rather smooth surface where the iron has dissolved away.

Corrosion of a condensate system can be inhibited by either mechanical or chemical means, although neither is completely effective when used alone. Nearly all modern boiler systems are protected by a combination of the two. Mechanical elimination of all avenues of air and process fluid in-leakage is an essential part of system protection. Feed water oxygen can be completely eliminated by mechanical deaeration plus the use of a chemical oxygen scavenger. In addition, various pretreatment processes such as hot lime softening, dealkylization, or demineralization can be used to reduce or eliminate make-up water bicarbonates and carbonates. However, even with pretreatment to reduce potential $CO_2$, chemical inhibitors are usually necessary for complete protection.

Three basic types of chemical corrosion inhibitors are used for condensate corrosion control: neutralizing amines, filming amines, and oxygen scavengers/metal passivators.

Neutralizing amines are typically volatile, alkaline compounds that are added to either the boiler feed water or the steam supply systems. They function by volatilizing into the steam and re-dissolving in the condensate with the $CO_2$. The amines chemically neutralize any acid present in the system. They raise pH to a level at which the condensate is much less aggressive towards the metallic components of the system.

Most commercially available neutralizing amine condensate treatments are blends of various amines. The blends offer combinations of certain characteristics that are unique to each amine. The characteristics of greatest importance when selecting amines are volatility, acid neutralizing ability, and basicity. Every volatile substance in a boiler system, or similar type system, has a specific volatility or vapor to liquid distribution ratio. The distribution ratio is defined by:

$V/L$=Concentration in the Vapor or Steam Phase/Concentration in the Liquid or Condensate Phase The distribution ratio indicates the portion of a given amine that will condense with the condensate or stay with the steam in a given piece of equipment. To neutralize $CO_2$, the amine must be in the condensate as the $CO_2$ dissolves.

Another very important criterion for amine choice is acid neutralizing ability. This is the amount of amine required on a weight basis to neutralize the carbonic acid present. The amine reacts with the carbonic acid in solution to form an amine bicarbonate:

$$RNH_2 + H^+ + HCO_3^- \rightarrow RNH_3^+ + HCO_3^- \qquad \text{(Equation 5)}$$

Although Equation 5 is for a primary amine, secondary and tertiary amines are also used for condensate treatment.

Once all of the acid in the condensate system has been neutralized (at a pH of about 8.3), amine basicity becomes important. Any additional amine added to the condensate system will hydrolyze, raising the condensate pH:

$$RNH_2 + H_2O \rightarrow RNH_3^+ + OH^- \qquad \text{(Equation 6)}$$

Basicities of neutralizing amines also vary. Above a certain pH, additional quantities of the weaker neutralizing amines do little to further increase the pH.

Neutralizing amine programs are most effective when fed to maintain a condensate pH of from about 8.5 to about 9.5, a range of maximum corrosion protection for both ferrous and copper alloys. Because the amines are added to the system in direct proportion to the amount of $CO_2$ in the steam, high alkalinity feed water requires considerable amounts of amine to obtain the desired pi range. The cost of such a program may be prohibitive and alternative means of corrosion protection may be desired.

Filming amines are high molecular weight amines with long-chain hydrocarbon alkyl groups. The amine-containing end of the molecule chemisorbs to the metal surfaces of the condensate system while the hydrophobic tail of the molecule extends away from the metal surface. A monomolecular, non-wettable film is thereby created on all metal surfaces that come into contact with condensate containing the filming amine. This film acts as a physical barrier between metal surfaces and corrosive condensate, offering protection against $CO_2$. Unlike neutralizing programs, filming amines protect the condensate system from $O_2$ attack. Since filming amines react with the metal surface instead of with a dissolved corrosive species, their feed rates are not directly proportional to the amount of contaminate (such as $O_2$ and $CO_2$) in the steam. Instead, the amount of filming amine required is related to the system's surface area.

The protective amine film is generally quite stable, but extreme pH conditions (high or low) may cause it to strip off the metal surfaces. Filming amines must be fed continuously to ensure that no gaps in protection occur in any parts of the system. However, excessive feed may cause the filming amine to accumulate as sticky masses in receivers, traps, valves, or any collection point. Therefore, periodic field testing is required to maintain a specified amount of filming amine in the condensate to avoid such deposits.

An alternative to filming amines for dissolved oxygen corrosion inhibition in condensate systems is the use of volatile oxygen scavengers in combination with neutralizing amines. The scavenger reacts directly with any oxygen present while the neutralizer provides protection from $CO_2$ corrosion. Such programs are controlled by the same parameters as neutralizing amine programs.

Examples of amines that are commonly added to boiler water systems include: diethylaminoethanol; morpholine; methoxypropyl amine; cyclohexyl amine; monoethanol amine; methyl amine; ethyl amine; propyl amine; butyl amine; t-butyl amine; octadecyl amine; and, mixtures of these amines.

SUMMARY OF THE INVENTION

The invention is a reagent useful in detecting the presence of primary amines, ammonia, or mixtures thereof. The reagent comprises:

a. from about 650 ppm to about 25 percent by weight of phthalic dicarboxyaldehyde;

b. from about 74 to about 99.88 percent by weight of an alkali metal borate; and, c. from about 550 ppm to about 22 percent by weight of a nucleophile.

DESCRIPTION OF THE PREFERRED EMBODIMENTS

Figure 1:
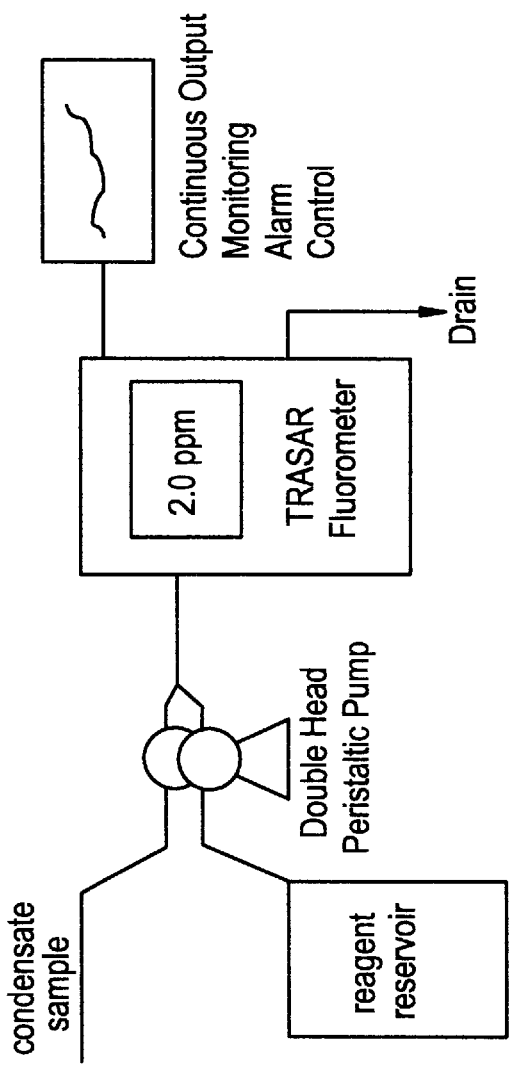
FIG. 1: A schematic drawing of an on-line monitoring system.

The invention is a reagent useful in detecting the presence of primary amines, ammonia, or mixtures thereof. The reagent comprises:

a. from about 650 ppm to about 25 percent by weight of phthalic dicarboxyaldehyde;

b. from about 74 to about 99.88 percent by weight of an alkali metal borate; and, c. from about 550 ppm to about 22 percent by weight of a nucleophile.

The reagent can be formulated as a solid, the relative composition of the components being determined by many factors, such as sample volume and pH, identity and concentration of analyte (primary amines and/or ammonia). The absolute concentrations and relative amounts of phthalic dicarboxyaldehyde and nucleophile will depend on the anticipated analyte range and the ratio of sample volume to reagent volume.

One would be able to formulate a useful reagent considering the above mentioned factors as well as the following requirements: the buffer must be of a sufficient concentration so that the pH of the final mixture of the sample and the reagent is maintained at the desired pH; the phthalic dicarboxyaldehyde should be present at a molar concentration in the final mixture of the sample and the reagent equal to or up to 1000 times greater than the molar concentration of the analyte; the nucleophile should also be present at a molar concentration in the final mixture of the sample and the reagent equal to or up to 1000 times greater than the molar concentration of the analyte; and, a minimal amount of methanol or other water miscible alcohols can be used to aid in the initial dissolution of the phthalic dicarboxyaldehyde.

The more preferred range of the phthalic dicarboxyaldehyde is from about 2 to about 20 percent by weight with the most preferred range being from about 7 to about 14 percent by weight. The more preferred range of the alkali metal borate used in the reagent is from about 75 to about 90 percent by weight with the most preferred range being from about 78 to about 85 percent by weight. The more preferred range of the nucleophile is from about 1 to about 18 percent by weight with the most preferred range being from about 6 to about 12 percent by weight.

The nucleophile can be selected from the group consisting of: cyanide; 2-mercaptoethanol; 3-mercaptopropionic acid; ethanethiol; methanethiol; thiolglycolic acid; and, alkali metal salts thereof.

For easier shipping and handling, the reagent may be packaged as a pre-measured solid or slurry. Such packaging may be accomplished in a tablet form, including pellets, of the reagent; a capsule, which includes dissolvable materials as well as moisture resistant materials; and, some type of an envelope container which can be made of paper or plastic that may or may not dissolve in the fluid sample being tested. An envelope container would also include a box or plastic bag.

Because some difficulty in dissolving the reagent may be experienced in some situations, the reagent can be dissolved in water, alcohol, or a mixture of water and alcohol to facilitate the mixing of the reagent with the fluid sample being tested. The preferred alcohols include methanol, ethanol, propanol, and isopropyl alcohol. A typical composition of the reagent dissolved in water, alcohol or a mixture of water and alcohol would be:

a. from about 12 ppm to about 3.3 percent by weight of phthalic dicarboxyaldehyde;

b. from about 0 to about 50 percent by weight of an alcohol;

c. from about 35 ppm to about 2 percent by weight of an alkali metal borate;

d. from about 10 ppm to about 5.4 percent by weight of a nucleophile; and, e. the balance being water.

The more preferred range of the phthalic dicarboxyaldehyde is from about 0.013 to about 1.3 percent by weight with the most preferred range being from about 0.13 to about 0.38 percent by weight. The more preferred range of the alkali metal borate used in the reagent is from about 0.037 to about 2 percent by weight with the most preferred range being from about 0.38 to about 2 percent by weight. The more preferred range of the nucleophile is from about 0.011 to about 2.2 percent by weight with the most preferred range being from about 0.11 to about 0.34 percent by weight. The more preferred range of the alcohol or alcohol/water mixture is from about 0.1 to about 45 percent by weight with the most preferred range being from about 1 to about 40 percent by weight.

The optimal reagent formulation varies with the desired analyte (primary amines, ammonia, or mixtures of primary amines and ammonia) range and with the ratio of sample volume to reagent volume. One should consider the above mentioned factors as well as the following requirements: the buffer must be of a sufficient concentration so that the pH of the final mixture of the sample and the reagent is maintained at the desired pH; the phthalic dicarboxyaldehyde should be present at a molar concentration in the final mixture of the sample and the reagent equal to or up to 1000 times greater than the molar concentration of the analyte; the nucleophile should also be present at a molar concentration in the final mixture of the sample and the reagent equal to or up to 1000 times greater than the molar concentration of the analyte; and, a minimal amount of alcohol or alcohol/water mixture can be used to aid in the initial dissolution of the phthalic dicarboxyaldehyde.

While a wide variety of nucleophiles would work in this reagent, the preferred nucleophiles are cyanide, 2-mercaptoethanol, 3-mercaptopropionic acid, ethanethiol, methanethiol, thiolglycolic acid, and alkali metal salts thereof.

For the reasons stated above, the reagent can be dissolved in water, alcohol, or a mixture of water and alcohol to facilitate the mixing of the reagent with the fluid sample being tested. The phthalic dicarboxyaldehyde may be dissolved in a small amount of water, alcohol, or a mixture of water and alcohol prior to the addition of the alkali metal borate and the nucleophile. The preferred alcohols include methanol, ethanol, propanol, and isopropyl alcohol.

Another embodiment of the invention is a reagent comprising:

a. from about 12 ppm to about 3.3 percent by weight of phthalic dicarboxyaldehyde;

b. from about 0 to about 50 percent by weight of an alcohol selected from the group consisting of: methanol; ethanol; propanol; and, isopropyl alcohol;

c. from about 35 ppm to about 2 percent by weight of an alkali metal borate;

d. from about 10 ppm to about 5.4 percent by weight of a nucleophile; and, e. the balance being water.

While a wide variety of nucleophiles would work in this reagent, the preferred nucleophiles are cyanide, 2-mercaptoethanol, 3-mercaptopropionic acid, ethanethiol, methanethiol, thiolglycolic acid, and alkali metal salts thereof.

Another embodiment of the invention is a method for producing a phthalic dicarboxyaldehyde containing reagent. The reagent is produced by:

a. forming a first homogeneous solution of from about 35 to about 99 percent by weight of water and from about 35 ppm to about 2 percent by weight of an alkali metal borate;

b. forming a second homogeneous solution of from about 0 to about 50 percent by weight of an alcohol selected from the group consisting of: methanol; ethanol; propanol; and, isopropyl alcohol, and from about 12 ppm to about 3.3 percent by weight of phthalic dicarboxyaldehyde;

c. mixing the first solution and the second solution to form a third homogeneous solution; and, d. adding to the third solution from about 10 ppm to about 5.4 percent by weight of a nucleophile selected from the group consisting of: cyanide; sulfite; 2-mercaptoethanol; 3-mercaptopropionic acid; ethanethiol; methanethiol; thiolglycolic acid; and, alkali metal salts thereof to the homogenous solution, the reagent.

The more preferred range of the phthalic dicarboxyaldehyde is from about 0.013 to about 1.3 percent by weight with the most preferred range being from about 0.13 to about 0.38 percent by weight. The more preferred range of the alkali metal borate used in the reagent is from about 0.037 to about 2 percent by weight with the most preferred range being from about 0.38 to about 2 percent by weight. The more preferred range of the nucleophile is from about 0.011 to about 2.2 percent by weight with the most preferred range being from about 0.11 to about 0.34 percent by weight. The more preferred range of the alcohol or alcohol/water mixture is from about 0.1 to about 45 percent by weight with the most preferred range being from about 1 to about 40 percent by weight.

The reagent can be used for detecting primary amines, ammonia, or mixtures thereof in an aqueous fluid. Aqueous fluid, as used herein, includes; aqueous fluid that may contain small amounts of hydrocarbons or other impurities; oil in water emulsions, both with and without continuous aqueous phase; latex; paper furnish; or any other fluid that contains water as one of the major constituents.

While the reagent can be used to detect the presence of, and ultimately determine the concentration of primary amines, ammonia, and mixtures of primary amines and ammonia, by varying the reaction times, the pH of the reagent, and the wavelengths used to measure the fluorescence, the method can be made selective for only primary amines or ammonia, at the exclusion of detecting the other group of compounds.

Ammonia reacts with the reagent at a slower rate than do the primary amines. Varying the time that the reagent is left in contact with the ammonia and primary amines contained in the fluid sample before the analysis is carried out determines whether the ammonia is detected or not. Varying the pH of the reagent also changes the sensitivity of the reagent toward the primary amines and ammonia. At a higher pH, the reagent is more sensitive to ammonia while at a lower pH, the reagent is more sensitive to primary amines. The pH of the reagent may range from a pH of about 8.5 to about a pH of about 12. The pH of the reagent may be varied by simply adding NaOH or similar caustic material to the reagent or to the first solution of the reagent. In addition, caustic material may need to be included as a component of the solid reagent or reagent slurry to obtain the desired pH of the final mixture of reagent and sample.

In addition, by varying the excitation and/or emission wavelengths at which the fluorescence is measured, the detection sensitivity of the reagent toward primary amines or ammonia is altered. By varying these three factors, the reagent can be used to detect the presence of and determine the concentration of either primary amines or ammonia separately, or when desired, a combination of the primary amines and ammonia in the fluid sample. Any interference from the compounds not being analyzed for is negligible.

One embodiment of the invention is a method for determining the presence and concentration of primary amines, ammonia, or mixtures thereof in a fluid, which may be an aqueous fluid. The method comprises the steps of:

a. obtaining a sample of a fluid;
b. adding to the fluid sample a reagent comprising:
  i. from about 650 ppm to about 25 percent by weight of phthalic dicarboxyaldehyde;
  ii. from about 74 to about 99.88 percent by weight of an alkali metal borate; and,
  iii. from about 550 ppm to about 22 percent by weight of a nucleophile,
  in an amount sufficient to react with all of the primary amines, ammonia, or mixtures thereof contained in the fluid sample;
c. measuring the fluorescence emission of the fluid sample containing the reagent at a known set of excitation and emission wavelengths;
d. comparing the fluorescence emission measured in step c. with a calibration curve obtained from fluorescence emissions at the same wavelength from at least two test fluid samples containing differing known amounts of primary amines, ammonia, or mixtures thereof; and then,
e. determining the presence and concentration of primary amines, ammonia, or mixtures thereof in the fluid.

The more preferred range of the phthalic dicarboxyaldehyde is from about 2 to about 20 percent by weight with the most preferred range being from about 7 to about 14 percent by weight. The more preferred range of the alkali metal borate used in the reagent is from about 75 to about 90 percent by weight with the most preferred range being from about 78 to about 85 percent by weight. The more preferred range of the nucleophile is from about 1 to about 18 percent by weight with the most preferred range being from about 6 to about 12 percent by weight.

The actual dosage of the reagent added to a fluid sample depends upon the fluid and upon the concentrations of the primary amines and ammonia in the fluid. The initial dosage of the reagent can be based on the expected levels or on an estimate of the concentrations of the primary amines and ammonia. This is especially true in the case of a boiler water system. Primary amines are added to the boiler water system to elevate the pH of the condensate. Based upon the amounts of primary amines added to the system, an estimate of concentrations can be made.

While a wide variety of nucleophiles would work in this reagent, the preferred nucleophiles are cyanide, 2-mercaptoethanol, 3-mercaptopropionic acid, ethanethiol, methanethiol, thiolglycolic acid, and alkali metal salts thereof.

For the reasons stated above, the reagent can be dissolved in water, alcohol, or a mixture of water and alcohol to facilitate the mixing of the reagent with the fluid sample being tested. The phthalic dicarboxyaldehyde may be dissolved in a small amount of water, alcohol, or a mixture of water and alcohol prior to the addition of the alkali metal borate and the nucleophile. The preferred alcohols include methanol, ethanol, propanol, and isopropyl alcohol.

The reagent, substantially non-fluorescent, in the presence of primary amines, ammonia, or mixtures thereof, apparently forms a fluorescent species that can be detected. In some situations, the fluid containing primary amines, ammonia, or mixtures thereof may be substantially non-fluorescent as compared to the fluid sample containing the reagent and primary amines, ammonia, or mixtures thereof which is fluorescent. However, the detection of the presence and the determination of the concentrations of the primary amines, ammonia, and mixtures thereof can be accomplished by other means of analysis which are discussed below.

Based upon the determination of the presence and concentration of the primary amines, ammonia, or mixtures thereof in the fluid, the concentration of the primary amines, ammonia, or mixtures contained in the fluid can be adjusted.

For easier shipping and handling, the reagent may be packaged as a pre-measured solid or slurry. Such packaging may be accomplished in a tablet, including pellet, form of the reagent; a capsule, which includes dissolvable materials as well as moisture resistant materials; and, some type of an envelope container which can be made of paper or plastic that may or may not dissolve in the fluid sample being tested. An envelope container would also include a box or plastic bag.

Because some difficulty in dissolving the reagent may be experienced in some situations, the reagent can be dissolved in water, alcohol, or a mixture of water and alcohol to facilitate the mixing of the reagent with the fluid being tested. As discussed above, the phthalic dicarboxyaldehyde may be dissolved in a small amount of water, alcohol, or a mixture of water and alcohol prior to the addition of the alkali metal borate and the nucleophile. The preferred alcohols include methanol, ethanol, propanol, and isopropyl alcohol.

One advantage of the invention is that the determination can be performed without isolating the primary amines, ammonia, or mixture of primary amines and ammonia in a fluid. As an example, a blend of several amine compounds are added to a boiler water system to elevate the pH of the condensate. While only one of the amine compounds is a primary amine, a sample of the boiler water may be treated with the reagent and the analysis completed on the primary amine without further processing the boiler water or removing the other amine compounds. Based on determinations of ratios of the other amine compounds to the primary amine, the concentration of the primary amine can be used to calculate the concentrations of the other amine compounds or the total amine concentration.

The invention has a wide variety of applications for testing fluid samples. The typical fluid system may be a cooling water system, a boiler water system and other heat transfer systems, ammonia production systems, bodily fluid systems, as well as an ion exchange system. In addition, this invention may be useful in testing bodily fluids for the presence of amino acids and proteins.

In both the production of ammonia and use of ammonia in refrigeration systems, ammonia leaks into the heat transfer equipment are problematic. Damage to the equipment as well as the reduced production of ammonia or the replacement cost of ammonia refrigerant advocates frequent checks of the water systems for ammonia.

Another embodiment of the invention is a method for determining the presence and concentration of primary amines, ammonia, or mixtures thereof in a fluid comprising the steps of:

a. obtaining a sample of a fluid;
 b. adding to the fluid sample a reagent comprising:
   i. from about 12 ppm to about 3.3 percent by weight of phthalic dicarboxyaldehyde;
   ii. from about 0 to about 50 percent by weight of an alcohol selected from the group consisting of; methanol; ethanol; propanol; and, isopropyl alcohol;
   iii. from about 35 ppm to about 2 percent by weight of an alkali metal borate;
   iv. from about 10 ppm to about 5.4 percent by weight of a nucleophile;
   v. the balance being water,
   in an amount sufficient to react with all of the primary amines, ammonia, or mixtures thereof contained in the fluid sample;
 c. measuring the fluorescence emission of the fluid sample containing the reagent at a known set of excitation and emission wavelengths;
 d. comparing the fluorescence emission measured in step c. with a calibration curve obtained from fluorescence emissions at the same wavelength from at least two test fluid samples containing differing known amounts of primary amines, ammonia, or mixtures thereof; and then,
 e. determining the presence and concentration of primary amines, ammonia, or mixtures thereof in the fluid. The fluid being tested may be an aqueous fluid.

The more preferred range of the phthalic dicarboxyaldehyde is from about 0.013 ppm to about 1.3 percent by weight with the most preferred range being from about 0.13 to about 0.38 percent by weight. The more preferred range of the alkali metal borate used in the reagent is from about 0.037 to about 2 percent by weight with the most preferred range being from about 0.38 to about 2 percent by weight. The more preferred range of the nucleophile is from about 0.011 to about 2.2 percent by weight with the most preferred range being from about 0.11 to about 0.34 percent by weight. The more preferred range of the alcohol or alcohol/water mixture is from about 0.1 to about 45 percent by weight with the most preferred range being from about 1 to about 40 percent by weight.

While a wide variety of nucleophiles would work in this reagent, the preferred nucleophiles are cyanide, 2-mercaptoethanol, 3-mercaptopropionic acid, ethanethiol, methanethiol, thiolglycolic acid, and alkali metal salts thereof.

The concentration of the primary amines, ammonia, or mixtures thereof contained in the fluid being tested may be adjusted based upon the determination of the presence and concentration of the primary amines, ammonia, or mixtures of primary amines and ammonia in the fluid sample. One advantage of the invention is that the determination can be performed without isolating the primary amines, ammonia, or mixture of primary amines and ammonia contained in the fluid. The fluid samples that may be tested using this method are those contained in a fluid system selected from the group consisting of: cooling water system; boiler water system; and, an ion exchange system.

Another embodiment of the invention is a method of monitoring and controlling feed of primary amines, ammonia, or a mixture thereof to a fluid system by monitoring the concentration of the primary amines, ammonia, or a mixture thereof by fluorescence analysis. The method comprises the steps of:

a. obtaining a sample of a fluid;
 b. adding to the fluid sample an effective amount of a reagent comprising:
   i. from about 650 ppm to about 25 percent by weight of phthalic dicarboxyaldehyde;
   ii. from about 74 to about 99.88 percent by weight of an alkali metal borate; and,
   iii. from about 550 ppm to about 22 percent by weight of a nucleophile,
   in an amount sufficient to react with all to react with all of the primary amine, ammonia, or mixtures thereof contained in the fluid sample;
 c. measuring the fluorescence emission of the fluid sample containing the reagent by fluorescence analysis of the fluid sample;
 d. determining the fluorescence emission magnitude at at least one fluorescence emission wavelength;
 e. comparing the fluorescence emission magnitude measured in step d. with the fluorescence emission magnitude obtained at the wavelength determined in step c. from at least two test fluid samples containing differing known amounts of primary amines, ammonia, or mixtures thereof;
 f. determining the concentration of primary amines, ammonia, or mixtures thereof in the fluid; and then,
 g. controlling the concentration of the primary amines, ammonia, or mixtures thereof in the fluid,
thereby monitoring and controlling the concentration of the primary amines, ammonia, or mixtures thereof within a pre-determined range in the fluid system. It is understood that one of the test fluids samples may contain no amines or ammonia.

The more preferred range of the phthalic dicarboxyaldehyde is from about 2 to about 20 percent by weight with the most preferred range being from about 7 to about 14 percent by weight. The more preferred range of the alkali metal borate used in the reagent is from about 75 to about 90 percent by weight with the most preferred range being from about 78 to about 85 percent by weight. The more preferred range of the nucleophile is from about 1 to about 18 percent by weight with the most preferred range being from about 6 to about 12 percent by weight.

A feed pump can be activated or its pumping rate increased to add additional primary amine, ammonia, or mixtures of primary amines and ammonia into the fluid system based upon the concentration of primary amine and ammonia found in the fluid.

The feed pump can also be deactivated or its pumping rate reduced to terminate or decrease the addition of primary amine, ammonia, or mixtures of primary amines and ammonia into the fluid system based upon the concentration of primary amine and ammonia found in the fluid.

The dilution of the fluid system can also be activated to reduce the concentration of primary amine, ammonia, or primary amines and ammonia contained in the fluid based upon the concentration of primary amine and ammonia found in the fluid. In addition, the dilution of the fluid system could be decreased to increase concentration.

Several different methods by which the concentration of the primary amines, ammonia, or mixture thereof can be measured are described below.

Fluorescence Emission Spectroscopy

The detection and quantification of specific substances by fluorescence emission spectroscopy is founded upon the proportionality between the amount of emitted light and the amount of a fluorescing substance present. When energy in the form of light, including ultra violet and visible light, is directed into a sample cell, fluorescent substances therein will absorb the energy and then emit that energy as light having a longer wavelength than the absorbed light. The amount of emitted light is determined by a photodetector. In practice, the light is directed into the sample cell through an optical light filter so that the light transmitted is of a known wavelength or spectrum of wavelengths, which is referred to as the excitation wavelength and generally reported in nanometers ("nm"). The emitted light is similarly screened through a filter so that the amount of emitted light is measured at a known wavelength or a spectrum of wavelengths, which is referred to as the emission wavelength and generally also reported in nanometers. When the measurement of specific substances or categories of substances at low concentrations is desired or required, such as often is the case for the process of the present invention, the filters are set for a specific combination of excitation and emission wavelengths, selected for substantially optimum low-level measurements.

Fluorescence emission spectroscopy is one of the preferred analysis techniques for the process of the present invention. Some naturally fluorescent compounds are also water treatment agents, and thus may be among the normal components of cooling water or boiler water, such as aromatic organic corrosion inhibitors, such as aromatic (thio) (tri)azoles.

In general for most fluorescence emission spectroscopy methods having a reasonable degree of practicality, it is preferable to perform the analysis without isolating in any manner the fluorescent indicator. Thus, there may be some degree of background fluorescence. In instances where the background fluorescence is low, the relative intensities (measured against a standard fluorescent compound at a standard concentration and assigned a relative intensity for instance 100) of the fluorescence of the indicator or compound of interest is very high versus the background, for instance a ratio of 100/10 or 500/10 when certain combinations of excitation and emission wavelengths are employed even at low fluorescent compound concentrations, and such ratios would be representative of relative performance (under like conditions) of respectively 10 and 50. For most cooling water or boiler water backgrounds, a compound that has a relative performance (fluorescence of tracer or compound of interest versus background) of at least about 5 at a reasonable concentration is very suitable as a fluorescent tracer itself or as a fluorescent concentration indicator. When there is or may be a specific chemical species of reasonably high fluorescence in the background, the indicator and the excitation and/or emission wavelengths often can be selected to nullify or at least minimize any interference to the indicator measurements(s) caused by the presence of such species.

Continuous on-stream monitoring of chemical tracers by fluorescence emission spectroscopy and other analysis methods is described in U.S. Pat. No. 4,992,380, B. E. Moriarity, J. J. Hickey, W. H. Hoy, J. E. Hoots and D. A. Johnson, issued Feb. 12, 1991, incorporated herein by reference.

Combined HPLC-Fluorescence Analysis

The combination of high-performance liquid chromatograph ("HPLC") and fluorescence analyses of fluorescent indicators is a powerful measurement tool with the present invention, particularly when very low levels of the fluorescent indicator are present or the background fluorescence encountered would otherwise interfere with the efficacy of the fluorescence analysis. The HPLC-fluorescence analysis method allows the indicator compound to be separated from the fluid matrix and then the indicator concentration can be measured. The combination of HPLC and fluorescence analysis is particularly effective for measuring minute levels of indicator compound in highly contaminated fluids.

The HPLC method can also be effectively employed to separate an indicator compound or analyte from a fluid matrix for the purposes of then employing a fluorescence-detection method or a detection method other than fluorescence analysis, and such other tracer-detection methods include without limitation light absorbance, post-column derivatization, conductivity and the like.

The HPLC method can also be used to separate chemically different indicators that are reaction products of different analytes, thereby giving additional information on the concentration of each analyte independently.

Colorimetry And Spectrophotometry Analysis

Colorimetry or spectrophotometry may be employed to detect and/or quantify a chemical tracer or chemical indicator. Colorimetry is a determination of a chemical species from its ability to absorb ultraviolet or visible light. One colorimetric analysis technique is a visual comparison of a blank or standard solution (containing a known concentration of the indicator species) with that of a sample of the fluid being monitored. Another colorimetric method is the spectrophotometric method wherein the ratio of the intensities of the incident and the transmitted beams of light are measured at a specified wavelength by means of a detector such as a photocell or photomultiplier tube. Using a colorimetric probe, a fiber optic (dual) probe, such as a Brinkman PC-80 probe (570 nm filter), a sample solution is admitted to a flowcell in which the probe is immersed. One fiber optic cable shines incident light through the sample liquid onto a mirror inside the cell and reflected light is transmitted back through the sample liquid into a fiber optic cable and then to the colorimetric analyzer unit, which contains a calorimeter, by the other cable. The colorimeter has a transducer that develops an electrical analog signal of the reflected light characteristic of the indicator concentration. The voltage emitted by the transducer activates a dial indicator and a continuous line recorder printout unit. A set point voltage monitor may be employed to constantly sense or monitor the voltage analog generated by the calorimeter, and upon detection of a indicator signal, a responsive signal may be transmitted to a responsive treatment agent feed line to commence or alter the rate of feed. Such a colorimetric analysis technique and the equipment that may be employed therefor are described in U.S. Pat. No. 4,992,380, B. E. Moriarity, J. J. Hickey, W. H. Hoy, J. E. Hoots and D. A. Johnson, issued Feb. 12, 1991, incorporated hereinto by reference. Chemical tracers suitable for use in conjunction with a colorimetric technique include transition metals (discussed below) and substances which show light absorbance which is detectable from that of other species present in the system fluid or substances which react with color-forming reagents to produce light absorbance which is detectable from that of other species present in the system fluids.

Analytical techniques for detecting the presence and/or concentration of a chemical species without isolation thereof are within an evolving technology, and the above survey of reasonable analytical techniques for use in the process of the present invention may presently not even be exhaustive, and techniques equivalent to the above for the purposes of the present invention will likely be developed in the future.

A chemical species may be selected for a given process based on a preference for one or more analytical techniques, or an analytical technique may be selected for a given process based on a preference for one or more chemical indicators. In preferred embodiments, the chemical compound(s) selected as the indicator should be soluble in at least one, and more preferably in both, of the temperature-conditioning fluid and process fluid of the industrial process, at least at the concentration level(s) expected in the respective fluid.

The following examples are presented to describe preferred embodiments and utilities of the invention and are not meant to limit the invention unless otherwise stated in the claims appended hereto.

EXAMPLES

Experimental Procedures
A. Colorimetric Test

A colorimetric test for total amine concentrations was evaluated as a benchtop method. The method used involved the timed, sequential addition of four reagents which develop a color change in amine-containing solutions. Absorbance of the solutions was then tested using a spectrophotometer, e.g. Hach DR-2000. The absorbance value was then be related to the total amine concentration, after calibration with solutions of known amine concentration.

After generating a calibration curve using standard solutions of cyclohexylamine prepared in the laboratory, the method was then used to test total amine levels in steam condensate samples (See Tables I and II). A 5 ppm cyclohexylamine standard was used to ensure calibration during testing. Although literature sources indicated that this test would not be sensitive to ammonia, it was discovered that ammonia causes a significant positive interference. Separate testing confirmed the presence of ammonia in the samples.

The test method was modified so that the ammonia interference would be avoided. Samples tested for amines by gas chromatography were also tested using the modified procedure. The results of the gas chromatography analysis without the ammonia interference are included in Tables I and II.

B. Fluorescent Tests For Amines

Two reagents that react with amines to form fluorescent products were evaluated. One reagent, fluorescamine, commercially available from Aldrich Chemical Company (described below as method 1) was tested as a benchtop method. However, subsequent work in the laboratory showed that another reagent (described below as method 2) is superior for on-line analysis. While neither the amines used as condensate neutralizers nor the reagents are fluorescent, the product of the reaction between the amine and the reagent is highly fluorescent. When the reagent is added in excess, the amine is converted stoichiometrically to the fluorescent product and the intensity of the fluorescence is proportional to the original amine concentration.

Both reagents react exclusively with primary amines, i.e. amines containing only one nitrogen-carbon bond. Cyclohexylamine was the only primary amine present in the boiler system at one testing site. Cyclohexylamine accounts for about 70% of the total amine present in that system and was added in constant proportion to the other amine in the blend, morpholine. Monitoring cyclohexylamine would be sufficient for determining compliance to target amine concentrations in the steam because concentrations of the other amines will track the concentration of cyclohexylamine. However, this assumption should be confirmed during tests of the on-line monitoring system.

Total Amine Concentrations in Steam Condensate

The colorimetric test was used to test steam condensate samples from 15 test sites (see Table I) and 8 sample streams available in the water chemistry laboratory (see Table II). Due to the ammonia interference, some of the results obtained earlier on in the testing are reported as total amines plus ammonia. Total amines plus ammonia concentrations in these samples ranged from 1 to 3 ppm, averaging about 2 ppm.

As the colorimetric method was modified to remove the interference, the results of the modified test method were in agreement with the results from gas chromatography analysis, and results obtained were in very good agreement with the total amine concentrations expected based on amine feed rate and steaming rate. Total amine concentrations ranged from 1.4 to 2.1 ppm and averaged 1.8 ppm. The total amine values were consistent with those obtained by gas chromatography (Tables I and II). The detection limit for the gas chromatography method is about 1 ppm so the colorimetric method provides much better sensitivity and accuracy.

While the colorimetric method provided excellent results, it was tedious, requiring four separate reagents and very careful laboratory technique. For these reasons, the colorimetric method is not a good candidate for routine testing on site at steam generating facilities.

Direct Steam Humidification

Having measured the total amine levels in the steam condensate to be no more than 2 ppm, the amine concentration in the air of rooms that use this steam for direct humidification can be estimated. For a worst case scenario, it can be assumed that the relative humidity of the room air in the absence of steam humidification is 0%, and that the room is humidified to 60% relative humidity using steam which itself contains 2 ppm total amine. At 60% relative humidity, the room would contain 10.8 mm Hg of water vapor, giving air that is 0.98% water by weight. Since this water vapor contains 2 ppm of total amine, the resultant total amine concentration in the room air would be 19 ppb.

In reality however, the ambient relative humidity is much higher, and much less steam would be used to reach the desired relative humidity, causing the actual airborne amine concentration to be much lower. In our calculations, we assumed no amine loss due to adsorption or reaction, which is believed to be the primary fate of amines introduced to a room in the steam humidification process. For example, researchers have determined experimentally that at 43% relative humidity, as much as 89% of cyclohexylamine is removed from the air by adsorption onto surfaces, again suggesting that our calculation gives an overestimation of the airborne amine concentration. The calculated total airborne amine concentration of 19 ppb can be thought of as an upper limit, whereas the actual amine air concentration is probably much lower. Since both the OSHA Personal Exposure Limits (PEL) and the Threshold Limit Values (TLV) are 20 ppm for morpholine and 10 ppm for cyclohexylamine, the value we estimate for total amine concentration is orders of magnitude smaller. Furthermore, since the odor thresholds for morpholine and cyclohexylamine are 140 ppb and 900 ppb, respectively, it is not possible to smell these amines in the air at a total concentration of 19 ppb.

Fluorescent Method I

The reagent tested on the benchtop performed well but suffered from interference from ammonia. Amine concentration results tracked the results from the colorimetric method (Tables I and II) but were consistently higher than those of the colorimetric method. The fluorescent method was calibrated with a standard solution of 5 ppm cyclohexylamine which also gave a 5 ppm result in the colorimetric test. Since the standard solution produced a consistent reading, it is believed that there is a species in the condensate that causes a positive interference for the fluorescent method. This species is almost certainly ammonia which does produce a positive interference for the fluorescent method.

Another problem was also noted with the reagent. The development of the fluorescence is very pH sensitive and the buffer used as a component of the reagent was only strong enough to control pH in unfixed condensate samples. Blowdown samples read anomalously high because the final pH was too high. Acid fixed samples did not react with the reagent because the pH was too low. Adjusting the pH of the solution before reagent addition solved the problem.

Fluorescent Method 2 On-Line Monitoring

Reviewing the investigations of on-line amine analysis methods, it was found that a method using the reagent as claimed in this application rather than the fluorescamine reagent screened in method I could be developed.

This reagent has many chemical and practical advantages over the first reagent. A schematic of the on-line monitoring system is shown in FIG. 1.

For on-line monitoring the reagent used in method 2 is dissolved to form a homogeneous water/alcohol solution and is contained in a plastic reservoir. A double headed peristaltic pump mixes the reagent and the sample stream in a constant proportion. The reaction between the amine and the reagent occurs in seconds to produce the fluorescent product. The combined sample and reagent stream containing the fluorescent reaction product then flows through the optical cell of a fluorometer.

The fluorometer is specially configured to optimize detection of the fluorescent amine reaction product. The fluorescence intensity is directly proportional to the amine concentration.

Figure 2:
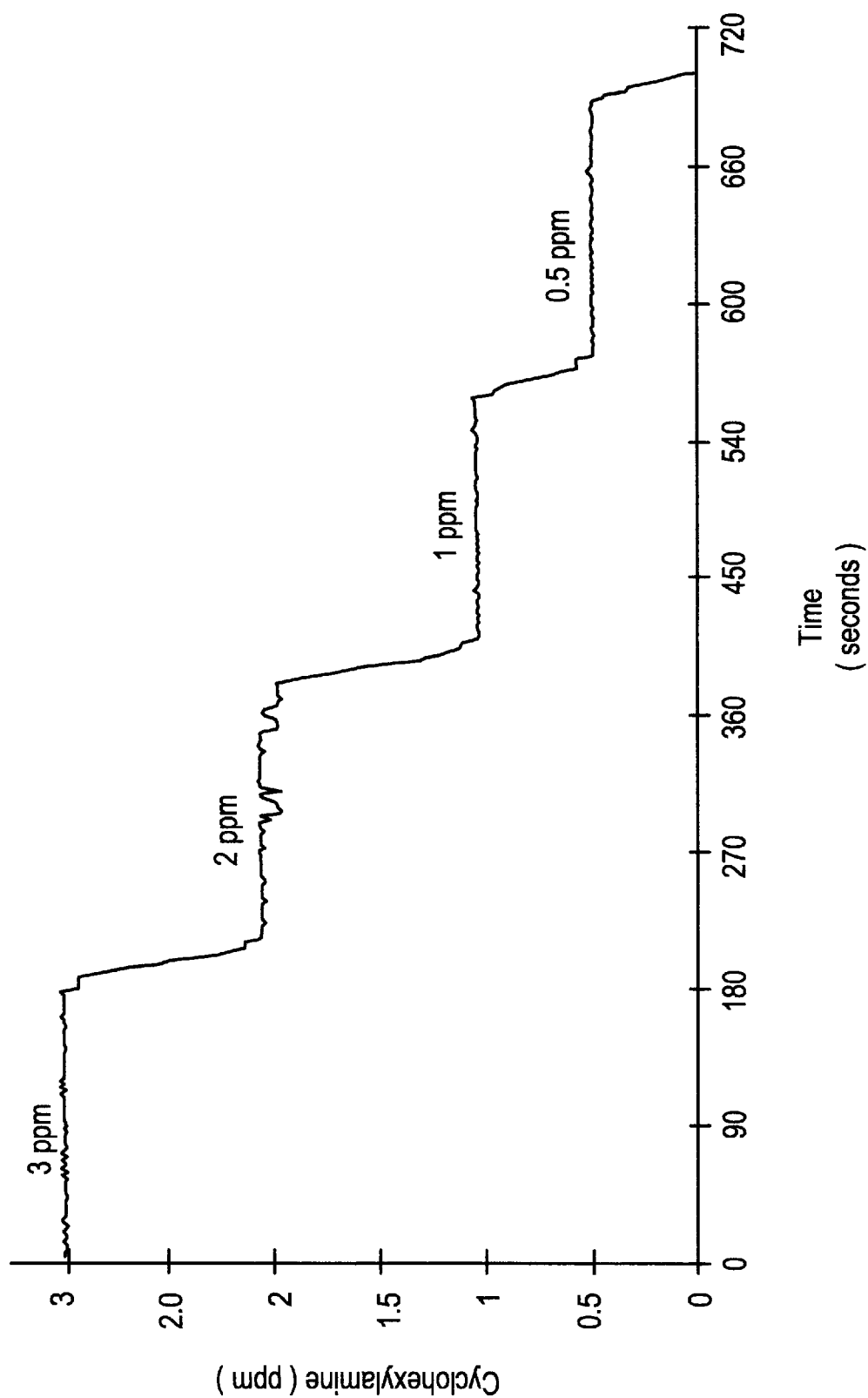
FIG. 2: A line graph showing the detection of cyclohexylamine at different concentrations.
Figure 3:
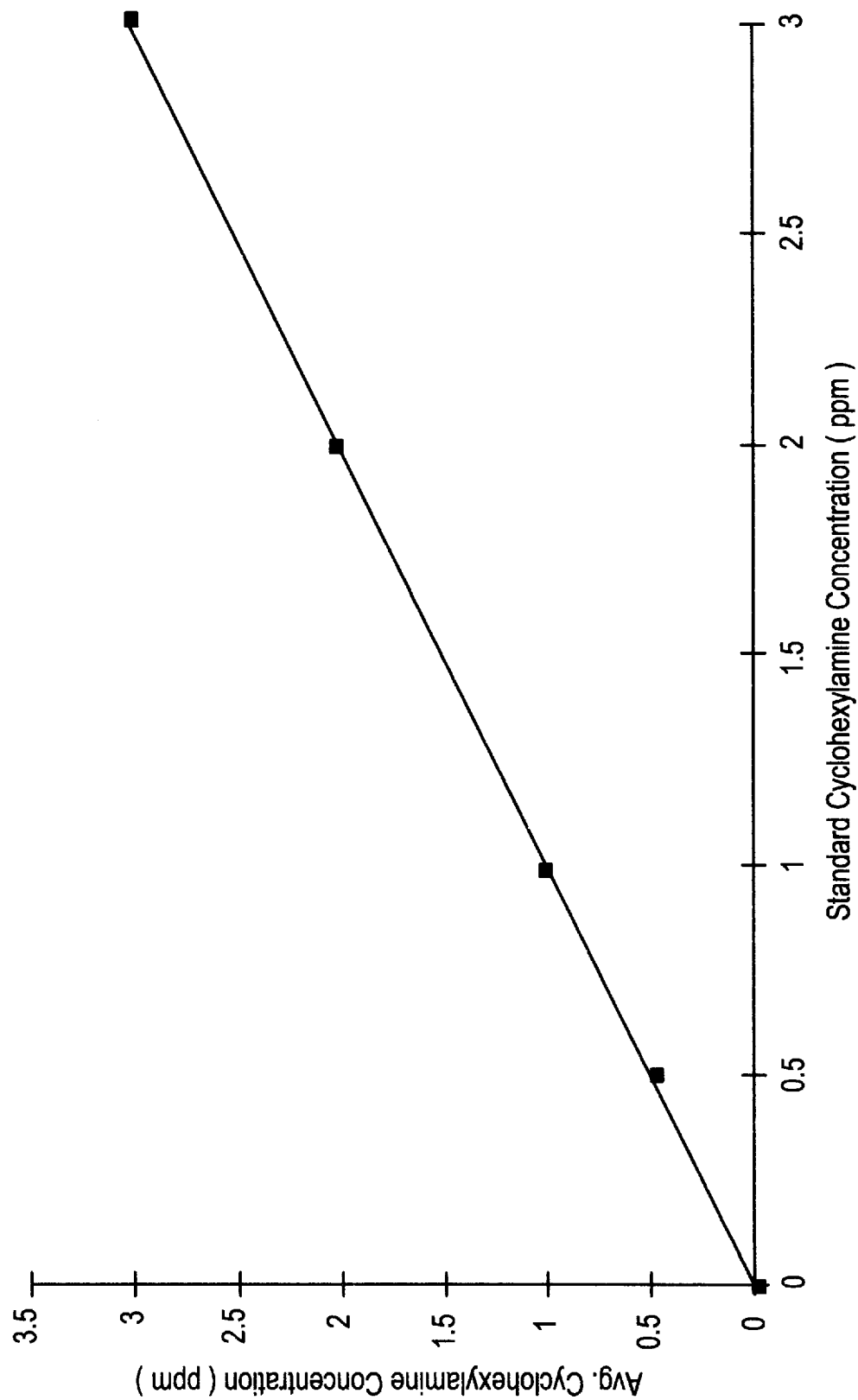
FIG. 3: A line graph comparing on-line measurements to standard concentrations of cyclohexylamine.
Figure 4:
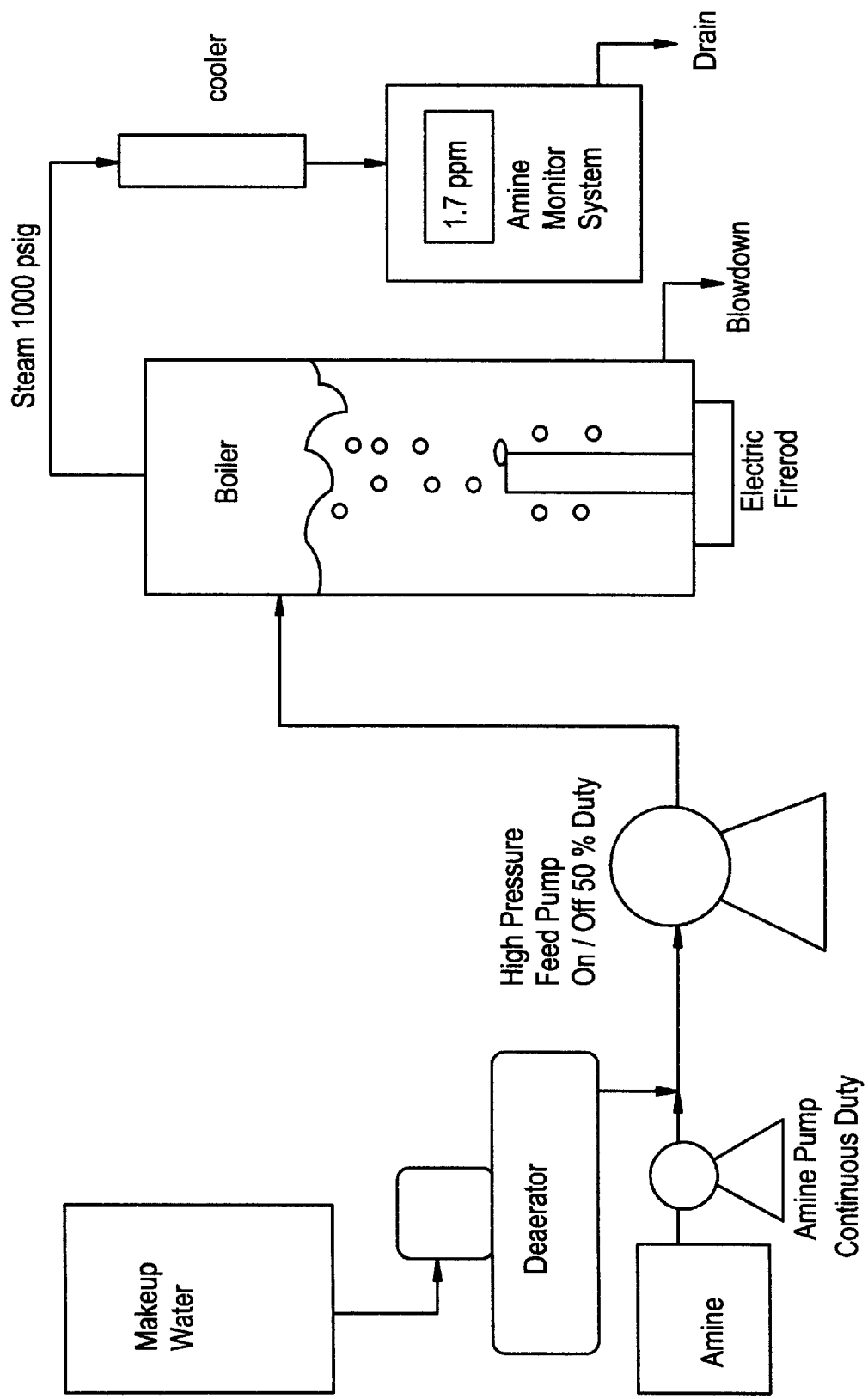
FIG. 4: A schematic drawing of experimental boiler equipment for on-line amine monitoring.
Figure 5:
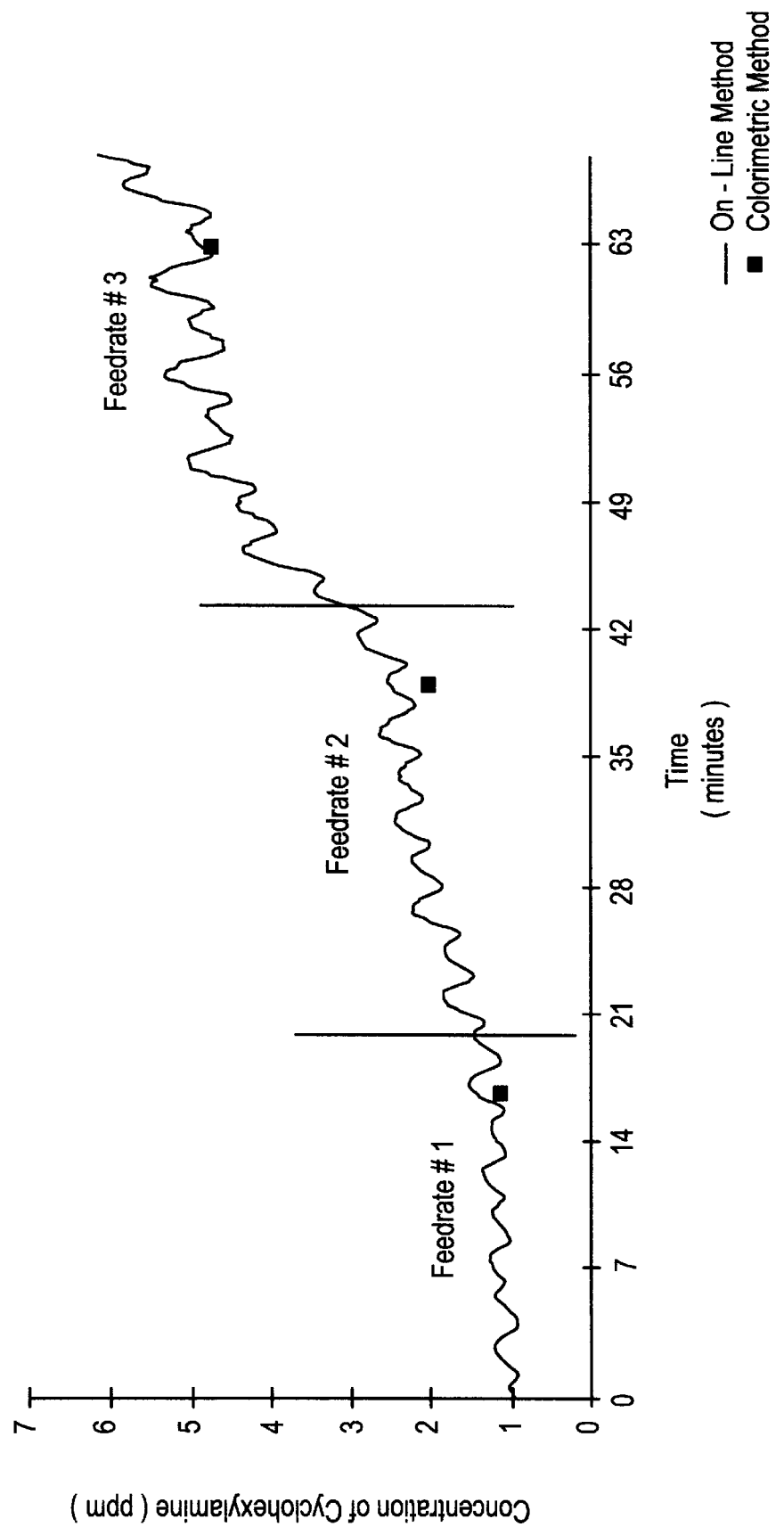
FIG. 5: A line graph showing a real time trace of cyclohexylamine concentration in steam.

A demonstration of on-line amine analysis is shown in FIG. 2. In this example a series of standard solutions of cyclohexylamine were used as the sample stream. FIG. 3 shows the excellent linear response of the method. Another experiment was performed by feeding cyclohexylamine to the feed water of an electric test boiler and analyzing for the amine in the steam condensate. FIG. 4 shows the equipment schematic for this experiment. The real time trace of cyclohexylamine concentration in the steam is shown in FIG. 5.

Figure 6:
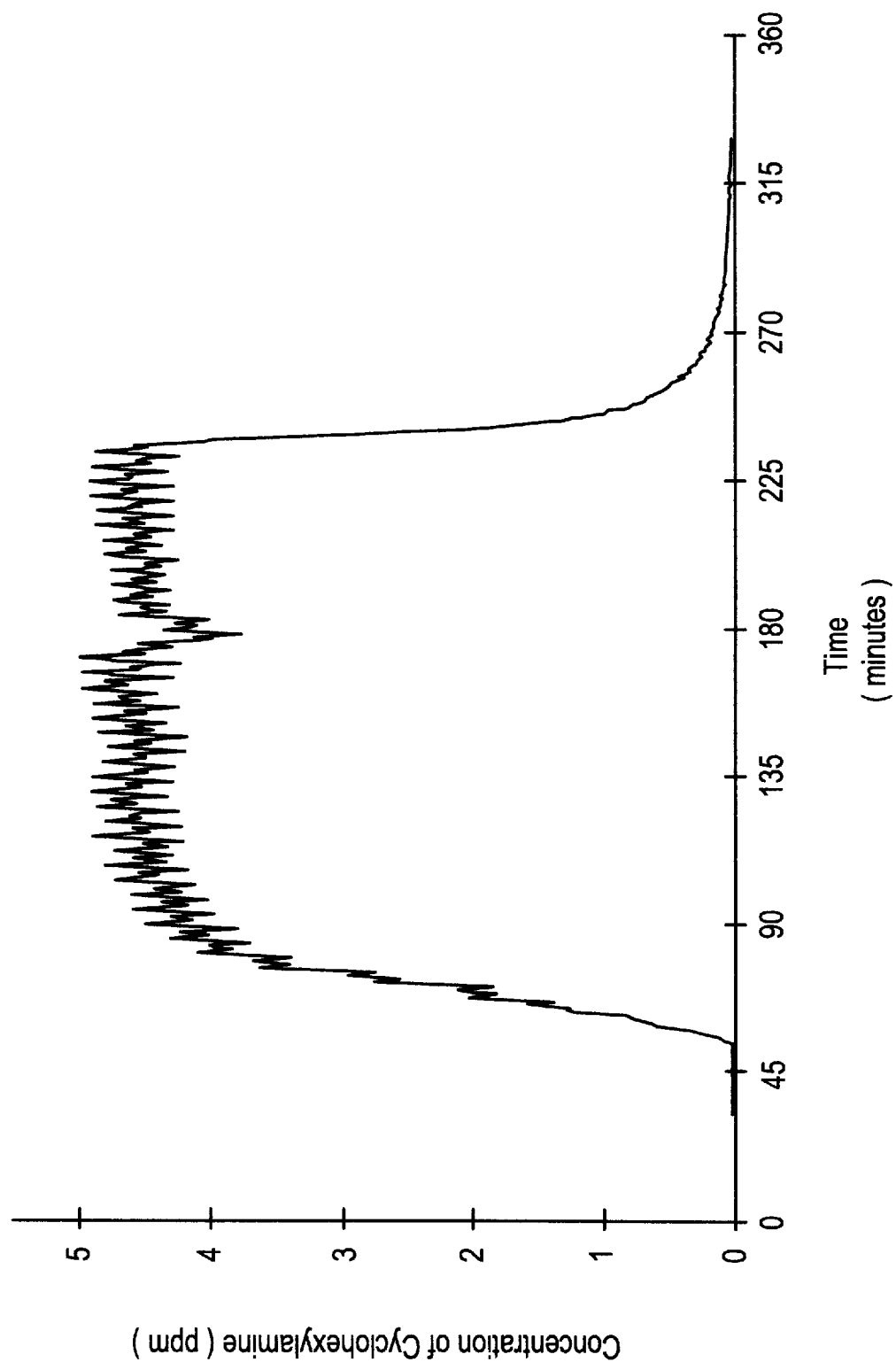
FIG. 6: A line graph showing a real time trace of cyclohexylamine concentration in steam.

It was found that cyclic fluctuations in amine concentration could be detected. These fluctuations were caused by the amine injection pump which ran at a constant feed rate while the high pressure feed water pump ran discontinuously based on the boiler water level. The amine injection pump was operated at three different rates during the experiment. Grab samples taken during each feed rate and analyzed with the colorimetric test confirm the average concentration of amine in the condensate, FIG. 5. FIG. 6 shows a longer experiment where the amine feed pump was turned on and then off.

The fluorescent on-line monitoring method provides a low-maintenance, real-time indicator of amine concentrations.

TABLE I

Results of Analysis for Amine

| Sample Point | Colorimetric Method Total Amine and Ammonia (ppm) | Colorimetric Method Total Amine (ppm) | Fluorescent Method #1 CHA(ppm) | GC Morpholine (ppm) | GC CHA (ppm) | GC DEAE (ppm) |
|---|---|---|---|---|---|---|
| Condensate pH Probe | 1.5 | | 1.8 | | | |
| Day 2 | 2.0 | | 2.0 | | | |
| Day 3 | 1.5 | | | | | |
| #2 DA Outlet Day 1 | 2.2 | | 2.3 | | | |

TABLE I-continued

Results of Analysis for Amine

| Sample Point | Colorimetric Method Total Amine and Ammonia (ppm) | Colorimetric Method Total Amine (ppm) | Fluorescent Method #1 CHA(ppm) | GC Morpholine (ppm) | GC CHA (ppm) | GC DEAE (ppm) |
|---|---|---|---|---|---|---|
| Day 2 | 1.8 | | 2.5 | | | |
| Day 3 | 2.2 | | | | | |
| #2 FW Day 1 | 1.9 | | 2.3 | | | |
| Day 2 | 2.7 | | 2.8 | | | |
| Day 3 | 2.4 | | | | | |
| #7 Continuous Blowdown Day 1 | 1.6 | | 21.5 | | | |
| Day 2 | 1.9 | | 23.5 | | | |
| Day 3 | 1.9 | | | | | |
| Mixed Bed Demineralizer Day 1 | 0.0 | | 0.4 | | | |
| Day 2 | 0.1 | | 0.5 | | | |
| Day 3 | 0.1 | | | | | |
| #7 Boiler Outlet Day 2 | 1.9 | | 2.1 | | | |
| Day 2 | 2.5 | | | | | |
| Turbine Generator Day 2 | 2.3 | | 2.3 | | | |
| Day 3 | 2.7 | | | | | |
| #3 Turbine Steam Inlet Day 2 | 1.8 | | 2.2 | | | |
| Day 3 | 2.7 | | | | | |
| Day 4 | 1.7 | 1.4 | | <1 | <1 | <1 |
| Day 5 | 2.6 | 2.1 | | <1 | 1 | <1 |
| Day 6 | 1.6 | 1.7 | | | | |
| Day 7 | 2.1 | 2.2 | | | | |

TABLE II

Results of Analysis for Amine

| Sample Point | Colorimetric Method Total Amine and Ammonia (ppm) | Colorimetric Method Total Amine (ppm) | Fluorescent Method #1 CHA(ppm) | GC Morpholine (ppm) | GC CHA (ppm) | GC DEAE (ppm) |
|---|---|---|---|---|---|---|
| Testing Site 1 | 2.2 | 1.8 | | <1 | <1 | <1 |
| Testing Site 2 | 2.2 | N/A | | <1 | 1 | <1 |
| Testing Site 3 | 1.9 | 1.7 | | <1 | 1 | <1 |
| Testing Site 4 | 2.1 | 1.8 | | <1 | 1 | <1 |
| Testing Site 5 | 2.3 | 1.8 | | <1 | <1 | <1 |
| Testing Site 6 | 2.0 | 1.9 | | <1 | <1 | <1 |
| Testing Site 7 | 0.8 | 1.9 | | <1 | <1 | <1 |
| Testing Site 8 | 2.0 | 1.5 | 2.4 | <1 | <1 | <1 |
| Testing Site 9 | 2.3 | 1.5 | | <1 | <1 | <1 |
| Testing Site 10 | 2.4 | 1.7 | | <1 | <1 | <1 |
| Testing Site 11 | 2.1 | 1.8 | | <1 | <1 | <1 |
| Testing Site 12 | 3.0 | 1.8 | 2.3 | <1 | <1 | <1 |
| Testing Site 13 | 1.7 | 1.9 | 2.6 | <1 | <1 | <1 |
| Testing Site 14 | 1.7 | 1.6 | 1.7 | <1 | <1 | <1 |
| Testing Site 15 | 1.9 | 2.0 | 0.5 | <1 | <1 | <1 |

Changes can be made in the composition, operation and arrangement of the method of the present invention described herein without departing from the concept and scope of the invention as defined in the following claims:

We claim:

1. A method for determining the presence and concentration of primary amines, ammonia, or mixtures thereof in an aqueous fluid comprising the steps of:

a. obtaining a sample of an aqueous fluid;
 b. adding to the fluid sample a reagent comprising:
   i. from about 650 ppm to about 25 percent by weight of phthalic dicarboxyaldehyde;
   ii. from about 74 to about 99.88 percent by weight of an alkali metal borate; and,
   iii. from about 550 ppm to about 22 percent by weight of a nucleophile, said nucleophile being thiolglycolic acid;
   in an amount sufficient to react with all of the primary amines, ammonia, or mixtures thereof contained in the fluid sample;
 c. measuring the fluorescence emission of the fluid sample containing the reagent at a known set of excitation and emission wavelengths;
 d. comparing the fluorescence emission measured in step c. with a calibration curve obtained from fluorescence emissions at the same wavelength from at least two test fluid samples containing differing known amounts of primary amines, ammonia, or mixtures thereof; and then, e. determining the presence and concentration of primary amines, ammonia, or mixtures thereof in the fluid.

2. The method according to claim 1, wherein the reagent is substantially non-fluorescent and the fluid sample containing the reagent and primary amines, ammonia, or mixtures thereof is fluorescent.

3. The method according to claim 1, wherein the fluid containing primary amines, ammonia, or mixtures thereof is substantially non-fluorescent and the fluid sample containing the reagent and primary amines, ammonia, or mixtures thereof is fluorescent.

4. The method according to claim 1, wherein the concentration of the primary amines, ammonia, or mixtures thereof contained in the fluid is adjusted based upon the determination of the presence and concentration of the primary amines, ammonia, or mixtures thereof in the fluid.

5. The method according to claim 1, wherein the reagent is packaged as a pre-measured solid or slurry.

6. The method according to claim 5, wherein the packaging is selected from the group consisting of: tablet; capsule; and, envelope.

7. The method according to claim 5, further comprising dissolving the reagent in water, alcohol, or a mixture thereof, forming a solution which is then added to the fluid sample.

8. The method according to claim 7, wherein the alcohol is selected from the group consisting of: methanol; ethanol; propanol; and, isopropyl alcohol.

9. The method according to claim 1, wherein the determination is performed without isolating the primary amines, ammonia, or mixture thereof contained in the fluid.

10. The method according to claim 1, wherein the fluid is contained in a fluid system selected from the group consisting of: cooling water system; boiler water system; and, an ion exchange system.

11. A method for determining the presence and concentration of primary amines, ammonia, or mixtures thereof in an aqueous fluid comprising the steps of:
   a. obtaining a sample of an aqueous fluid;
   b. adding to the fluid sample a reagent comprising:
      i. from about 12 ppm to about 3.3 percent by weight of phthalic dicarboxyaldehyde;
      ii. from about 0 to about 50 percent by weight of an alcohol selected from the group consisting of; methanol; ethanol; propanol; and, isopropyl alcohol;
      iii. from about 35 ppm to about 2 percent by weight of an alkali metal borate;
      iv. from about 10 ppm to about 5.4 percent by weight of a nucleophile, said nucleophile being thiolglycolic acid;
      v. the balance being water,
      in an amount sufficient to react with all of the primary amines, ammonia, or mixtures thereof contained in the fluid sample;
   c. measuring the fluorescence emission of the fluid sample containing the reagent at a known set of excitation and emission wavelengths;
   d. comparing the fluorescence emission measured in step c. with a calibration curve obtained from fluorescence emissions at the same wavelength from at least two test fluid samples containing differing known amounts of primary amines, ammonia, or mixtures thereof; and then,
   e. determining the presence and concentration of primary amines, ammonia, or mixtures thereof in the fluid.

12. The method according to claim 11, wherein the concentration of the primary amines, ammonia, or mixtures thereof contained in the fluid is adjusted based upon the determination of the presence and concentration of the primary amines, ammonia, or mixtures thereof in the fluid.

13. The method according to claim 11, wherein the determination is performed without isolating the primary amines, ammonia, or mixture thereof contained in the fluid.

14. The method according to claim 11, wherein the fluid is contained in a fluid system selected from the group consisting of: cooling water system; boiler water system; and, an ion exchange system.

15. A method of monitoring and controlling feed of primary amines, ammonia, or a mixture thereof to an aqueous fluid system by monitoring the concentration of the primary amines, ammonia, or a mixture thereof by fluorescence analysis comprising the steps of:
   a. obtaining a sample of an aqueous fluid;
   b. adding to the fluid sample an effective amount of a reagent comprising:
      i. from about 650 ppm to about 25 percent by weight of phthalic dicarboxyaldehyde;
      ii. from about 74 to about 99.88 percent by weight of an alkali metal borate; and,
      iii. from about 550 ppm to about 22 percent by weight of a nucleophile, said nucleophile being thiolglycolic acid
      in an amount sufficient to react with all of the primary amine, ammonia, or mixtures thereof contained in the fluid sample;
   c. measuring the fluorescence emission of the fluid sample containing the reagent by fluorescence analysis of the fluid sample;
   d. determining the fluorescence emission magnitude at least one fluorescence emission wavelength;
   e. comparing the fluorescence emission magnitude measured in step d. with the fluorescence emission magnitude obtained at the wavelength determined in step c. from at least two test fluid samples containing differing known amounts of primary amines, ammonia, or mixtures thereof;
   f. determining the concentration of primary amines, ammonia, or mixtures thereof in the fluid; and then,
   g. controlling the concentration of the primary amines, ammonia, or mixtures thereof in the fluid,
thereby monitoring and controlling the concentration of the primary amines, ammonia, or mixtures thereof within a predetermined range in the fluid system.

16. The method according to claim 15, further comprising activating a feed pump or increasing the pumping rate of a feed pump to add additional primary amine, ammonia, or mixtures thereof into the fluid system based upon the concentration of primary amine, ammonia, or mixtures thereof in the fluid determined in step f.

17. The method according to claim 15, further comprising deactivating a feed pump or decreasing the pump rate of a feed pump to decrease the addition of primary amine, ammonia, or mixtures thereof into the fluid system based upon the concentration of primary amine, ammonia, or mixtures thereof in the fluid determined in step f.

18. The method according to claim 15, further comprising activating dilution of the fluid system to reduce the concentration of primary amine, ammonia, or mixtures thereof in the fluid based upon the concentration of primary amine, ammonia, or mixtures thereof in the fluid determined in step f.

* * * * *